United States Patent
Helmer

(10) Patent No.: US 12,303,269 B2
(45) Date of Patent: May 20, 2025

(54) DEVICE FOR MANAGING A MEDICATION REGIME

(71) Applicant: Sanofi, Paris (FR)

(72) Inventor: Michael Helmer, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/509,688

(22) Filed: Nov. 15, 2023

(65) Prior Publication Data

US 2024/0164680 A1    May 23, 2024

Related U.S. Application Data

(63) Continuation of application No. 17/879,840, filed on Aug. 3, 2022, now Pat. No. 11,857,325, which is a
(Continued)

(30) Foreign Application Priority Data

Dec. 11, 2017 (EP) .................................. 17306738

(51) Int. Cl.
  *A61B 5/18*   (2006.01)
  *A61B 5/00*   (2006.01)
  *A61B 5/15*   (2006.01)

(52) U.S. Cl.
  CPC .............. *A61B 5/18* (2013.01); *A61B 5/0002* (2013.01); *A61B 5/150801* (2013.01);
(Continued)

(58) Field of Classification Search
  CPC ... A61B 5/18; A61B 5/0002; A61B 5/150801; A61B 5/4839; A61B 5/6893; A61B 5/7264
(Continued)

(56) References Cited

U.S. PATENT DOCUMENTS 6,075,755 A  *  6/2000  Zarchan ................. G16H 10/65
                                                    368/10
6,480,744 B2 * 11/2002  Ferek-Petric ...... A61N 1/37258
                                                    340/576
(Continued)

FOREIGN PATENT DOCUMENTS

CN        101143234       3/2008
CN        102369029       3/2012
(Continued)

OTHER PUBLICATIONS

International Search Report and Written Opinion in International Appln. No. PCT/EP2018/083847, dated Feb. 4, 2019, 11 pages.
(Continued)

*Primary Examiner* — Zhen Y Wu
(74) *Attorney, Agent, or Firm* — Fish & Richardson P.C.

(57) ABSTRACT

A device for communicating a driving ability level of a user, the device comprising at least a processor, a memory, and a wireless transceiver. The device is configured to: receive a communication from a medical device, wherein the communication comprises information relating to a condition of the medical device; and send a communication to a vehicle. The information relating to a condition of the medical device is processed in order to determine a driving ability level of the user by the assignment of a category selected from a group comprising a first category and a second category.

19 Claims, 9 Drawing Sheets

Related U.S. Application Data continuation of application No. 16/771,030, filed as application No. PCT/EP2018/083847 on Dec. 6, 2018, now Pat. No. 11,426,108.

(52) U.S. Cl.
CPC .......... *A61B 5/4839* (2013.01); *A61B 5/6893* (2013.01); *A61B 5/7264* (2013.01)

(58) Field of Classification Search
USPC ........................................................ 340/576
See application file for complete search history.

(56) References Cited

U.S. PATENT DOCUMENTS

| | | | |
|---|---|---|---|
| 6,697,732 B1 | 2/2004 | Gotfried | |
| 7,740,612 B2* | 6/2010 | Hochman | G09B 23/285 604/246 |
| 7,821,408 B2* | 10/2010 | Vancil | G16H 10/60 340/576 |
| 9,278,177 B2* | 3/2016 | Edwards | G16H 20/17 |
| 9,724,475 B2* | 8/2017 | Krulevitch | A61M 5/3129 |
| 10,773,032 B2* | 9/2020 | Cirillo | G01D 5/34 |
| 2005/0107673 A1* | 5/2005 | Ball | A61B 5/002 600/301 |
| 2006/0180378 A1* | 8/2006 | Nordin | B60K 28/063 180/271 |
| 2009/0030366 A1* | 1/2009 | Hochman | G16H 20/17 604/67 |
| 2010/0228193 A1 | 9/2010 | Wyrick | |
| 2011/0009821 A1* | 1/2011 | Jespersen | A61M 5/1452 604/131 |
| 2011/0313349 A1* | 12/2011 | Krulevitch | G16H 20/17 604/65 |
| 2013/0226372 A1* | 8/2013 | Kim | G16H 10/60 701/2 |
| 2013/0285816 A1* | 10/2013 | Sezanayev | G07C 9/00174 340/576 |
| 2014/0279707 A1* | 9/2014 | Joshua | G06Q 30/0283 701/1 |
| 2014/0296824 A1* | 10/2014 | Edwards | A61P 5/28 604/506 |
| 2015/0287257 A1 | 10/2015 | Thompson | |
| 2015/0359977 A1* | 12/2015 | Watanabe | A61J 7/0472 604/111 |
| 2015/0360617 A1* | 12/2015 | Schulz | B60W 30/06 340/576 |
| 2016/0019767 A1* | 1/2016 | Ebe | G08B 21/24 340/425.5 |
| 2016/0030683 A1* | 2/2016 | Taylor | A61M 5/345 604/151 |
| 2016/0129182 A1* | 5/2016 | Schuster | A61M 15/008 702/56 |
| 2016/0279335 A1* | 9/2016 | Sjöstedt | A61M 5/24 |
| 2016/0318521 A1* | 11/2016 | Nothacker | A61B 5/082 |
| 2017/0092030 A1* | 3/2017 | Badger, II | B60R 25/102 |
| 2017/0166054 A1* | 6/2017 | Ayala Rodriguez | A61B 5/07 |
| 2017/0305433 A1 | 10/2017 | Yoshi et al. | |
| 2017/0372011 A1 | 12/2017 | Noeth | |
| 2018/0015223 A1* | 1/2018 | Aeschlimann | A61M 5/24 |

FOREIGN PATENT DOCUMENTS

| | | |
|---|---|---|
| CN | 103167890 | 6/2013 |
| DE | 202009002550 | 7/2009 |
| EP | 2572740 | 3/2013 |
| JP | 2011-248850 | 12/2011 |
| JP | 2015-505253 | 2/2015 |
| WO | WO 2008/056128 | 5/2008 |
| WO | WO 2011/109303 | 9/2011 |
| WO | WO 2013/083715 | 6/2013 |
| WO | WO 2015/136513 | 9/2015 |
| WO | WO 2016/038498 | 3/2016 |
| WO | WO 2016/113126 | 7/2016 |

OTHER PUBLICATIONS

International Preliminary Report on Patentability in International Appln. No. PCT/EP2018/083847, dated Jun. 16, 2020, 8 pages.

* cited by examiner

DEVICE FOR MANAGING A MEDICATION REGIME

CROSS REFERENCE TO RELATED APPLICATIONS

The present application is a continuation of U.S. patent application Ser. No. 17/879,840, filed on Aug. 3, 2022, which is a continuation of U.S. patent application Ser. No. 16/771,030, filed on Jun. 9, 2020, now U.S. Pat. No. 11,426,108, which is the national stage entry of International Patent Application No. PCT/EP2018/083847, filed on Dec. 6, 2018, and claims priority to Application No. EP 17306738.0, filed on Dec. 11, 2017, the disclosures of which are incorporated herein by reference.

TECHNICAL FIELD

The present disclosure relates to a device and system configured to monitor the use of a medical device, such as an injection device, make an assessment of a user's impairment in relation to driving a vehicle and transmit information associated with the assessment.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing the dosage knob or an injection button of the insulin pen.

Alternatives to a disposable injection pens include connectable injection devices, such as drug pumps. For instance, insulin may be delivered by a drug pump. Other medical devices include meters for monitoring the condition of a patient, such as blood glucose meters or methods of indirectly measuring blood glucose levels, blood pressure monitors, pulse monitors, etc. Intelligent electronic pill boxes may be used to monitor the delivery of non-injectable medicaments.

Patients may fail to administer the correct quantity of the medicament, or follow the correct dosage regime. This can result in impairment of the patient. For instance, diabetic patients who have not following the correct medicament regime may experience fatigue, blurred vision, and/or confusion. Patients who require cardiovascular medicaments and patients who require pain medicament can become similarly impaired.

SUMMARY

To be able to monitor insulin injection, for instance to prevent false handling of the insulin pen or to keep track of the doses already applied, it is desirable to measure information related to a condition and/or use of the injection device, such as for instance information on the injected insulin dose.

According to an aspect of the disclosure, there is provided a device for communicating a driving ability level of a user, the device comprising at least a processor, a memory and a wireless transceiver, wherein the device is configured to: receive a communication from a medical device, wherein the communication comprises information relating to a condition of the medical device; and send a communication to a vehicle; wherein the information relating to a condition of the medical device is processed in order to determine a driving ability level of the user by the assignment of a category selected from a group comprising a first category and a second category.

The device may be configured to send the communication to the vehicle via a smart key associated with the vehicle. Alternatively, the device may be a smart key associated with the vehicle and storing a medical monitoring application.

The smart key may be configured to allow a user to access a vehicle and/or activate a vehicle.

The device may be a smartphone storing a medical monitoring application and an application for communication with the vehicle.

According to another aspect of the disclosure, there is provided a system comprising any device as disclosed herein, further comprising the electronic warning system of the vehicle.

The electronic warning system may be configured to: if the driving ability level of the user is assigned to the first category, not emit a warning signal; and if the driving ability level of the user is assigned to the second category, emit a warning signal.

The driving ability level of the user may be assigned to a category selected from the group further comprising a third category, and wherein the electronic warning system of the vehicle is further configured to: if the driving ability level of the user is assigned to the third category, prevent the starting of the engine of the vehicle or activate a safety assistant system.

The device may be configured to: if the driving ability level of the user is assigned to the second category, send a communication to a navigation system.

The device may be configured to: store information relating to a medication dose history of the user; determine, based on the stored medication dose history, a due time for a subsequent medication dose administration; and wirelessly transmit data representing the due time for the subsequent medication dose administration to a smart key associated with a vehicle or to an electronic warning system of a vehicle.

The device may be further configured to wirelessly communicate with an injection monitoring device and to receive dosing information from the injection monitoring device, the dosing information comprising a date, time and data representing an administered medicament dose.

The device may be further configured to update the stored medication dose history based on the received dosing information.

The device may be further configured to determine a driving ability level of the user by inferring the user's physiological condition based on a comparison of the current time with the due time for the subsequent medication dose administration.

The device may be a smartphone storing a medical monitoring application. There is provided a system comprising the aforementioned device and the smart key associated with a vehicle, wherein the smart key is configured to wirelessly transmit the data representing the due time for the subsequent medication dose administration to an electronic warning system of the associated vehicle. The smart key may be further configured to wirelessly transmit an indication of a driving ability level of the user to the electronic warning system of the associated vehicle. The smart key may be further configured to perform a plausibility check in response to receiving the data representing the due time for the subsequent medication dose administration, the plausibility check comprising confirming the received information with the smartphone. The smart key may be further configured to: transmit an unlock signal to the associated vehicle; in response to transmitting the unlock signal to the associated vehicle, compare the current time with the received data representing the due time for the subsequent medication dose administration; and communicate the result of the comparison to the electronic warning system of the associated vehicle. The smartphone and smart key may be part of a system which may further comprise the electronic warning system of the vehicle configured to: receive the result of the comparison of the current time with the due time for the subsequent medication dose administration; and if the current time is later than the due time, emit a warning signal. The electronic warning system of the vehicle may be further configured to: if the current time is later than the due time, prevent the starting of the engine of the vehicle.

Alternatively, the device may be a smart key associated with a vehicle, the smart key storing a medical monitoring application, and wherein the smart key is configured to wirelessly transmit the data representing the due time for the subsequent medication dose administration to an electronic warning system of the associated vehicle. The smart key may be further configured to wirelessly transmit an indication of a driving ability level of the user to the electronic warning system of the associated vehicle. The smart key may be further configured to perform a plausibility check in response to receiving the data representing the due time for the subsequent medication dose administration, the plausibility check comprising confirming the received information with the injection monitoring device. The smart key may be further configured to: transmit an unlock signal to the associated vehicle; in response to transmitting the unlock signal to the associated vehicle, compare the current time with the received data representing the due time for the subsequent medication dose administration; and communicate the result of the comparison to the electronic warning system of the associated vehicle. The smart key may be part of a system which may further comprise an electronic warning system configured to: receive the result of the comparison of the current time with the due time for the subsequent medication dose administration; and if the current time is later than the due time, emit a warning signal. The system may comprise the electronic warning system of the vehicle further configured to: if the current time is later than the due time, prevent the starting of the engine of the vehicle.

The aforementioned systems may further comprise a medical device. The systems may further comprise an injection monitoring device.

In an aspect, there is provided a system comprising any device as disclosed herein, and the electronic warning system of a vehicle, wherein the device is configured to: receive a communication from a medical device, wherein the medical device is a permanent monitoring device and the communication comprises information relating to a physiological condition of a user; wherein the information relating to a physiological condition of the user is processed in order to determine a driving ability level of the user by the assignment of a category selected from a group comprising a first category, a second category, and a third category; wherein the electronic warning system of the vehicle is configured to: if the driving ability level of the user is assigned to the third category, prevent the starting of the engine of the vehicle or activate a safety assistant system.

The activation of a safety assistant system may cause the vehicle to slow and/or stop.

DETAILED DESCRIPTION

In the following disclosure, embodiments will be described with reference to an insulin injection device. The present disclosure is however not limited to such application and may equally well be deployed with injection devices that eject other medicaments, or with any other kind of medical device, including drug pumps, meters for monitoring the condition of a patient, blood glucose meters, meters for indirectly measuring blood glucose level, blood pressure monitors, pulse monitors, intelligent electronic pill boxes, and the like.

Where a medical device is referred to this may refer to the medical device itself, or may refer to a supplementary device designed to attach to a medical device and to derive information from the medical device.

Where a condition of a medical device is referred to, this may refer to any condition referred to herein. The condition of the medical device includes but is not limited to: a date and time of medicament delivery, a quantity of medicament delivery, the type of medicament delivered, the identity of the medicament batch, the medicament expiry date, and any combination thereof. The condition of the medical device may also include but is not limited to: the information gathered or determined by the medical device, for instance blood glucose levels, blood pressure, pulse rate, or any combination thereof.

A smart key may be a device configured to allow a user to access a vehicle and/or activate a vehicle. Activating a vehicle may include starting an engine and/or activating the ignition.

Figure 1:
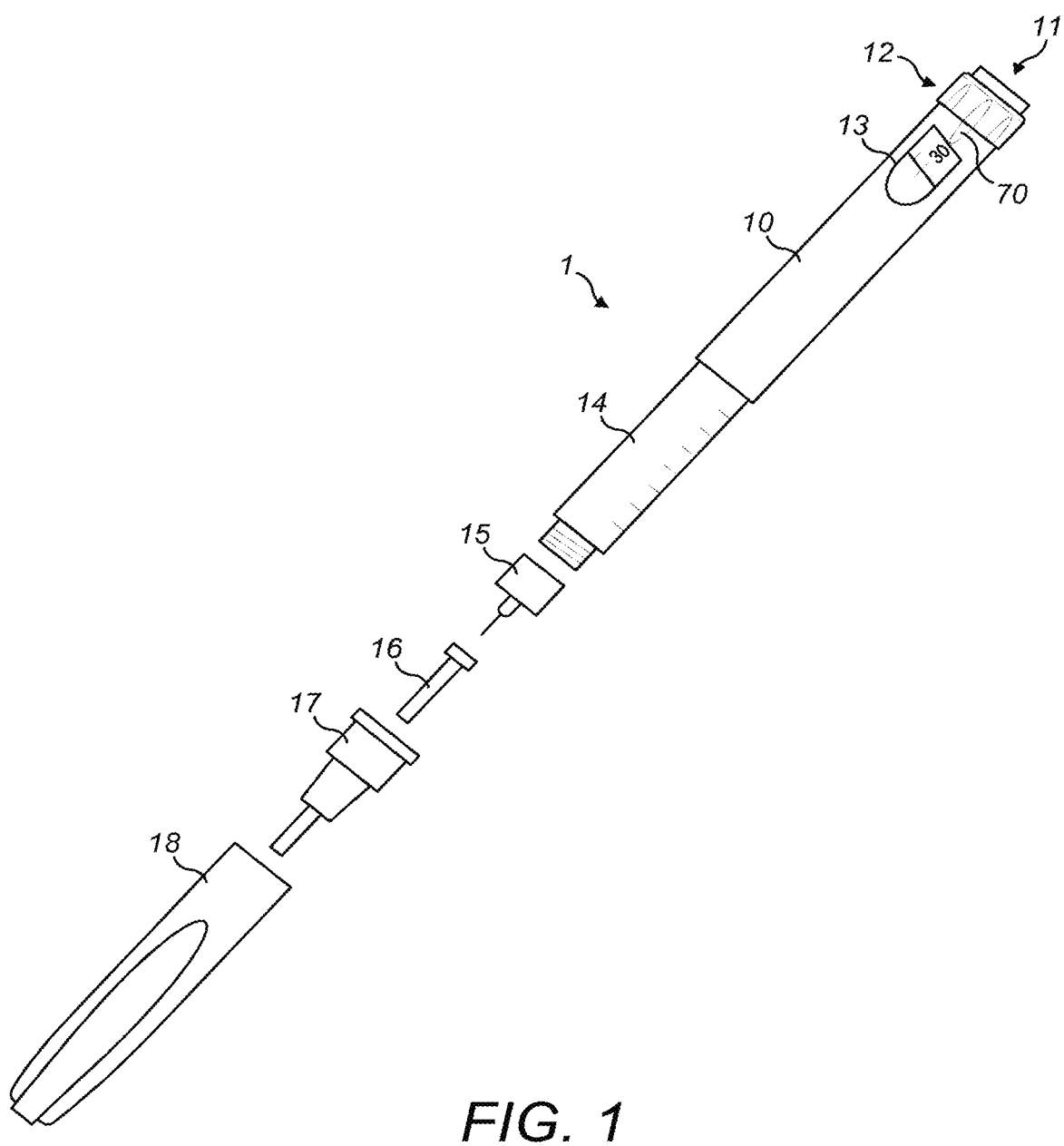
FIG. 1 shows an exploded view of an injection device.

FIG. 1 is an exploded view of an injection device 1, which may for instance represent Sanofi's Solostar® insulin injection pen or Sanofi's AllStar® insulin injection pen, however the present disclosure is also compatible with other types and makes of injection pens as described below.

The injection device 1 of FIG. 1 is a pre-filled, disposable injection pen that comprises a housing and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1. It should be noted that the selected dose may equally well be displayed differently. A label (not shown) is provided on the housing 10. The label includes information about the medicament included within the injection device, including information identifying the medicament. The information identifying the medicament may be in the form of text. The information identifying the medicament may also be in the form of a color. The information identifying the medicament may also be encoded into a barcode, QR code or the like. The information identifying the medicament may also be in the form of a black and white pattern, a color pattern or shading.

The dosage window 13 may be in the form of an aperture in the housing 10, which permits a user to view a limited portion of a number sleeve 70 that is configured to move when the dosage knob 12 is turned, to provide a visual indication of a currently programmed dose. Alternatively, the number sleeve 70 may remain stationary during the dose dialing phase, and the dosage window 13 may move as a dose is dialed in to reveal the number corresponding to the dialed dose. In either case, the number sleeve 70 may be a component which rotates when a dose is being dispensed from the injection device 1.

The injection device 1 may be configured so that turning the dosage knob 12 causes a mechanical click sound to provide acoustical feedback to a user. The number sleeve 70 mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose may also cause a mechanical click sound, which is however different from the sounds produced when using dosage knob 12. In some other embodiments, the injection device 1 does not have a separate injection button 11 and a user depresses the entire dosage knob 12, which moves longitudinally relative to the housing 10, in order to cause the medicament to be dispensed.

In the various embodiments, during delivery of the insulin dose, the dosage knob 12 is turned to its initial position in an axial movement, that is to say without rotation, while the number sleeve 70 is rotated to return to its initial position, e.g. to display a dose of zero units.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards. For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 2:
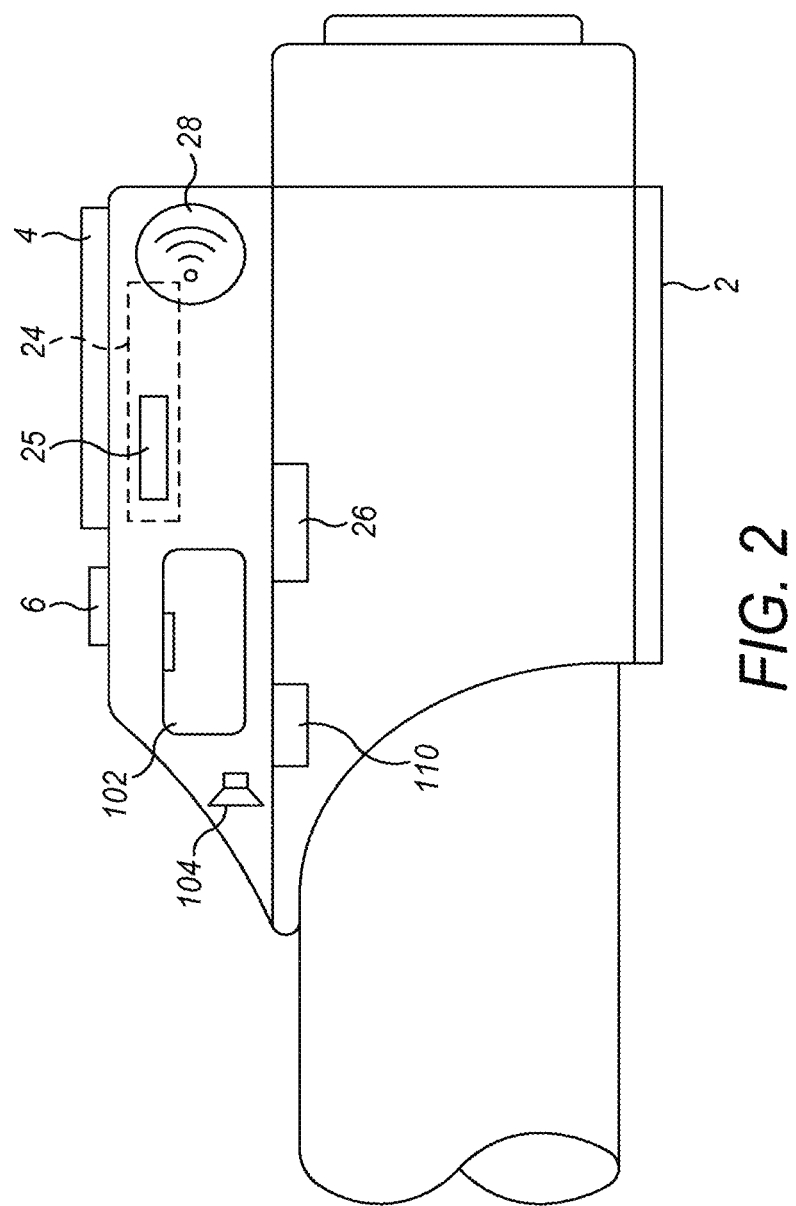
FIG. 2 depicts a data collection device, attached to the injection device of FIG. 1.

FIG. 2 shows an injection monitoring device 2 (also referred to as an add-on device, supplementary device or dosage monitoring device herein) according to some embodiments. The injection monitoring device 2 is configured to be releasably secured to the injection device 1 and is shown attached to the injection device 1 in FIG. 2. FIG. 2 illustrates some of the major internal and external components of the injection monitoring device 2. Externally, the injection monitoring device 2 comprises a display unit 4, a user input 6, and a battery compartment 102.

Internally, the injection monitoring device 2 comprises electronics 24. The electronics 24 comprise at least a processor 25 and memory. The electronics 24 may comprise both a program memory and a main memory. The processor 25 may for instance be a microprocessor, a Digital Signal Processor (DSP), Application Specific Integrated Circuit (ASIC), Field Programmable Gate Array (FPGA) or the like. The processor 25 executes program code (e.g. software or firmware) stored in the program memory, and uses a main memory, for instance to store intermediate results. The main memory may also be used to store a logbook on performed ejections/injections. The program memory may for instance be a Read-Only Memory (ROM), and the main memory may for instance be a Random Access Memory (RAM).

The injection monitoring device 2 also comprises a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fiber connection. When data is transmitted, the units of the data (values) transferred may be explicitly or implicitly defined. For instance, in case of an insulin dose, always International Units (IU) may be used, or otherwise, the used unit may be transferred explicitly, for instance in coded form. The transmitted data also includes a time stamp associated with an injection. The injection monitoring device 2 may also calculate, store and transmit other data relating to the user's medicament regime and resulting physiological condition.

The injection monitoring device 2 also comprises an audio module 104 configured to provide audio feedback to a user of the injection monitoring device 2. Both the wireless unit 28 and audio module 104 may be coupled to and controlled by the electronics 24.

The injection monitoring device 2 may also comprise an optical sensor 26 for reading information identifying the medicament. The information identifying the medicament may be the color of the housing 10 of the injection device, or the color of an area of the housing or a label affixed to the housing. In these embodiments, the optical sensor 26 may be a simple photometer configured to detect the color. In some other embodiments, the information identifying the medicament may be a QR code, or other similar encoded information and the optical sensor 26 may be a camera or QR code reader. Further, one or more light sources may be provided to improve reading of optical sensor 26. The light source may provide light of a certain wavelength or spectrum to improve color detection by optical sensor 26. The light source may be arranged in such a way that unwanted reflections, for example due to the curvature of the housing 10, are avoided or reduced. In an example embodiment, the optical sensor 26 is a camera unit configured to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance an expiration date). This code may be a QR code. The QR code is in general black and white and thus no color detection is required on the part of the optical sensor 26. This allows the optical sensor 26 to be simple and cheap to manufacture.

The processor 25 may be configured to check the information read by the optical sensor 26 against pre-stored information in order to verify that the user is injecting the correct medicament. If the processor 25 does not recognize the information or recognizes the information as indicating a different medicament to that which the user should be receiving at that time, then the injection monitoring device 2 may produce an alarm signal. The alarm signal may comprise words or graphics displayed on the display unit 6 or sound produced by the audio module 104. Alternatively, or in addition, the injection monitoring device 2 may send an alarm signal to an external device via wireless unit 28.

The injection monitoring device 2 comprises an injection device status sensor 110 (also referred to herein as a non-contact sensor or first non-contact sensor). The status sensor 110 may take a number of forms. The status sensor 110 is configured to output signals indicative of the positions of one or more components within the injection device 1. The status sensor 110 may be referred to as a non-contact sensor, since it is able to sense the absolute position and/or movement of components within the injection device 1 without contact between the sensor 110 and any of the components sensed. The electronics 24 receive these signals and infer an operational state of the injection device 1 and cause information regarding the timing of the operation of the injection device 1 to be recorded in the main memory and/or transmitted to an external device via the wireless unit 28.

The exact position of the status sensor 110 within the injection monitoring device 2 depends upon the position and movement range of the moveable component of the injection device being measured. The moveable component may be close to the cylindrical part of the housing 10 of the injection device 1. Therefore, the status sensor 110 is positioned adjacent the cylindrical part of the housing 10.

The status sensor 110 may be an optical sensor configured to observe the number sleeve 70 through the window 13 and thereby to read the dose dialed into the injection device 1. Alternatively, the status sensor 110 may be an infrared sensor and the injection monitoring device 2 may comprise a separate infrared light source. The status sensor 110 may then observe the movement of components within the injection device 1 through an area of the housing 10, dosage knob 12 or injection button 11 which is opaque to visible light and infer the dialed or delivered dose of medicament from the observed movements. In some alternative embodiments, the status sensor 110 may use another non-contact sensing technology, such as capacitive displacement sensing, magnetic induction sensing or Eddy current sensing in order to measure the movement of the internal components of the injection device 1.

In any case, the injection monitoring device 2 measures the amount of medicament injected from the injection device 1 and records the dose history. In some embodiments, the injection monitoring device 2 is further configured to use the determined dose history and other stored information about the user of the injection device 1 to determine the due time and date for the user's next dose and/or the amount of the user's next dose.

Figure 3:
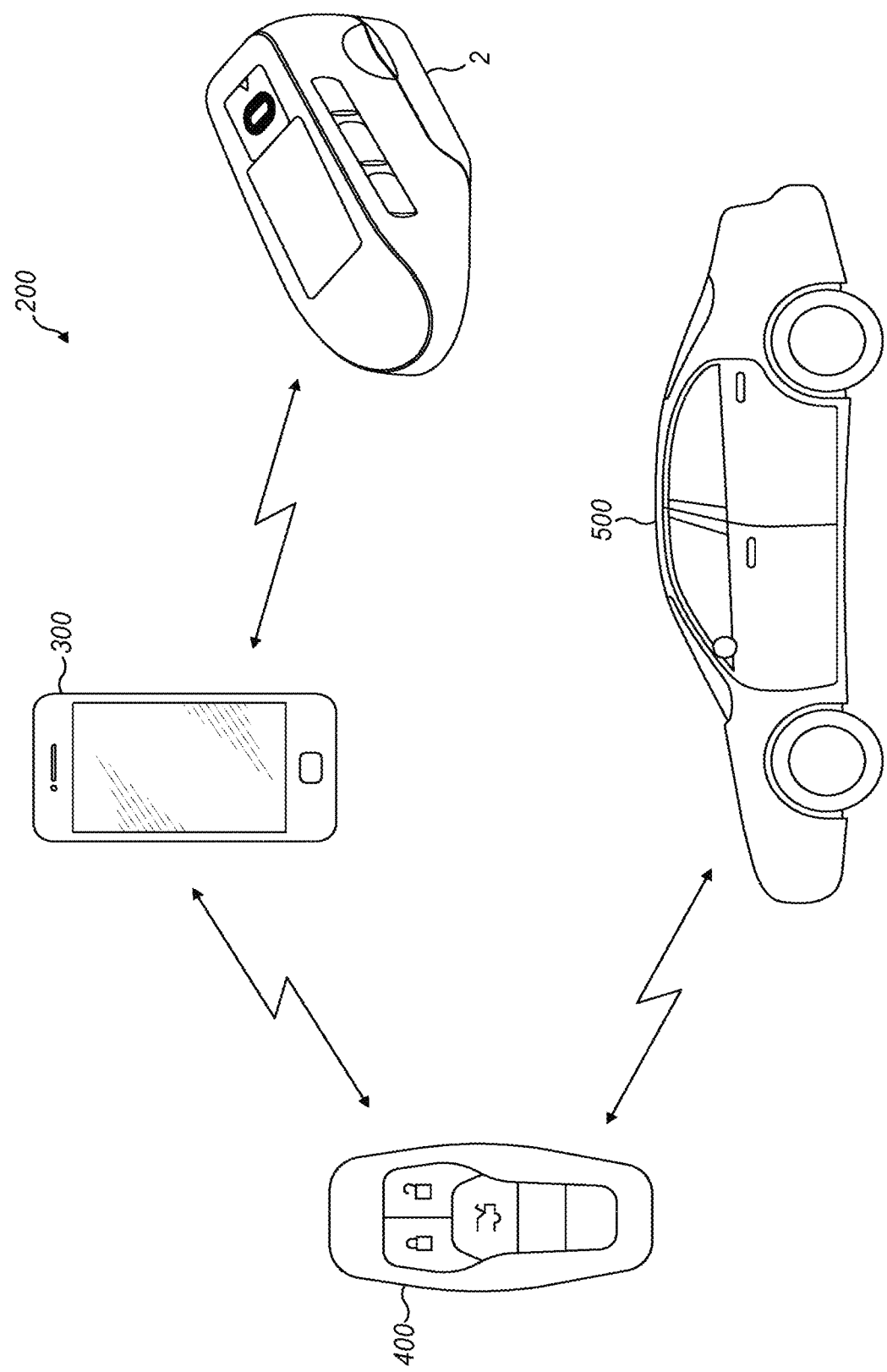
FIG. 3 is a schematic illustration of a system in which the present disclosure can be used.
Figure 4:
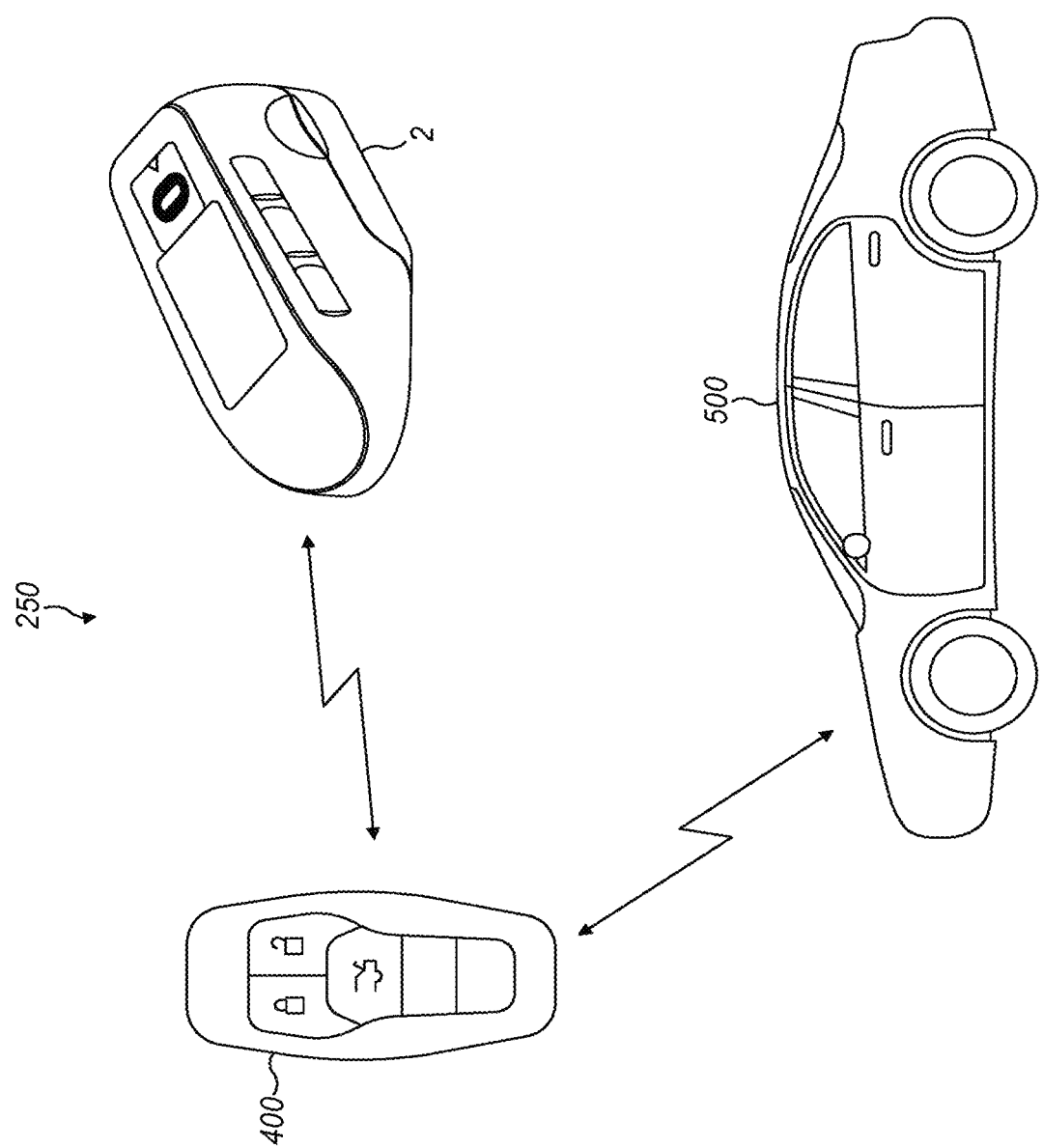
FIG. 4 is a schematic illustration of a different system in which the present disclosure can be used.

FIGS. 3 and 4 illustrate schematically two different systems in which the present disclosure can be used.

Referring firstly to FIG. 3, a system 200 is shown in which the injection monitoring device 2 communicates wirelessly with a device 300 for managing a medication regime of a user. The device 300 may for example be a smartphone storing a medical monitoring application. The medical monitoring application may be programmed to receive dosing information from the injection monitoring device 2, the dosing information comprising at least a date and time of the most recent injection and data representing the administered medicament dose. The injection device 2 may be configured to transmit the dosing information to the device 300 whenever a new injection is performed, or alternatively only in response to a user input.

The system 200 also comprises a smart key 400. The smart key 400 is configured to communicate wirelessly with the device 300. The smart key 400 is also configured to at least partially control and to communicate wirelessly with an associated vehicle 500. The vehicle 500 may comprise a number of electronic systems, for example related to locking/unlocking the vehicle and starting/stopping the vehicle. The vehicle 500 may also comprise an electronic warning system, configured to emit alerts under circumstances, or even to prevent the engine of the vehicle from being started.

Use of a smart key 400 as an interface between an external device and a vehicle 500 can increase the safety of the system. This is because at the point-of-delivery to the user the smart key 400 is already specific for the user's vehicle 500, and hence it is easier to include security systems to avoid, for instance, hacking. This may be important, as the vehicle 500 can include safety assistant systems described herein, which are capable of directly affecting the vehicle 500, for instance changing the vehicle's speed.

A second advantage is that users do not always connect third party devices, such as smartphones, to their vehicle. By including the smart key 400 within the system, it is possible to configure the system so that the user is forced to activate and/or connect the necessary devices.

The medical monitoring application on the device 300 stores and manages the user dose history. The medical monitoring application is configured to use the stored dose history to determine a due date and time for the user's next medication dose and/or dose volume/units. The medical monitoring application may also infer a physiological condition of the user by comparing the current time with the determined due time for the next medication dose. For example, where the user's medicament is insulin used to treat diabetes, if the medical monitoring application determines that the current time is later than the due time for the next dose, it may be inferred that the user's blood glucose levels are low. If the medical monitoring application determines that the current time is much later than the due time, for example later than a predetermined threshold, then it may be inferred that the user has hypoglycemia. The user's physiological condition may be expressed in terms of their fitness to drive a vehicle. This may also be referred to as a "wellness parameter" which may define the likely level of the user's impairment.

The medical monitoring application can control the device 300 to present information to the user, including the due date and time for their next medication dose administration and any warnings should the current time be later than the determined due date and time. The medical monitoring application may also be programmed to control the device 300 to transmit at least the determined due date and time for the user's next medication dose to the smart key 400. In some embodiments, the device 300 may also transmit an indication of the user's physiological condition and/or fitness to drive a vehicle.

Figure 9:
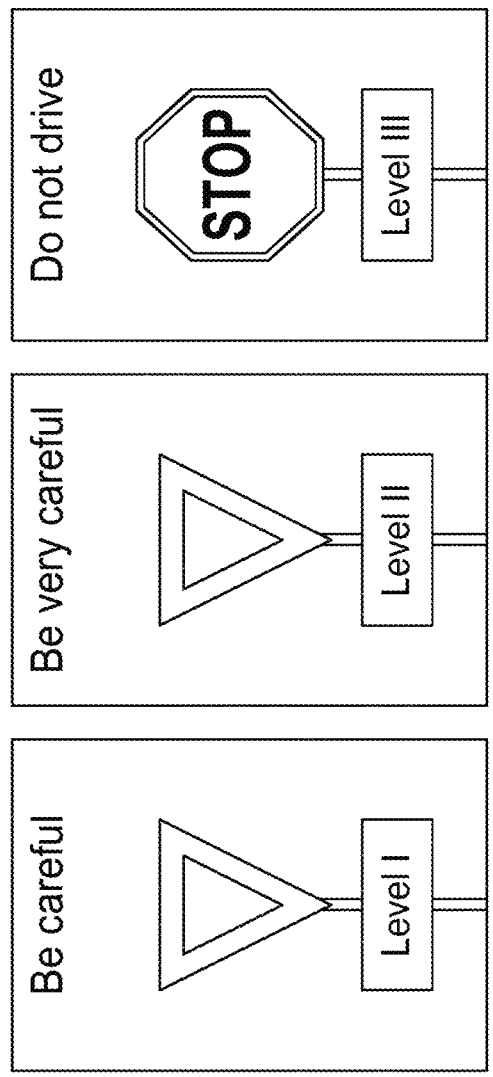
FIG. 9 shows examples of standardized symbols from pharmaceutical packaging suitable for use with the disclosed systems.

The smart key 400 receives and stores the due time for the user's next medication dose administration. Whenever the smart key 400 is in range of the vehicle 500, or alternatively whenever the smart key 400 is used to unlock the vehicle 500, the smart key communicates the due time to the electronic warning system of the vehicle 500. If the user's next dose is overdue (i.e. if the current time is later than the due time), the electronic warning system is configured to emit a warning. This warning may take a number of forms, for example an audible alarm, which may be a spoken communication, or a visual indication. The vehicle 500 may be provided with an internal display screen which may display warning text such as "Your next insulin dose is overdue and your ability to drive may be impaired". Additional traffic symbols or the standardized symbols from pharmaceutical packaging can also be used (FIG. 9).

In addition the display screen may specify when the user's next dose was due. The display screen may also indicate the severity of the user's potential impairment, for example using a scale of 1 to 3 and color coding, such as yellow, orange and red. In some embodiments, the electronic warning system only emits a warning when the vehicle is actually started, or it may emit a different warning when the vehicle is started, for example an audible warning.

The vehicle 500 may provide the user with advice, and this advice may be provided visually or audibly. For instance the internal display screen may advise a user who is inferred to be impaired based upon their dose history to take action to alleviate their condition. This advice can include instructions or a reminder to take a dose of medicament or to take any recommended steps.

The vehicle 500 may include a navigation system. When the navigation system is in use for navigation the system may calculate, based upon the due date and time for the next medication dose administration, a route that incorporates an appropriate stop allowing the user to administer their dose. The stop should be timed such that the user's fitness to drive is not impaired before the injection. The navigation system can be configured such that the stop is communicated to the user and the user is informed that a medicament dose should be administered. If the navigation system is not in use for navigation, the system may indicate, based upon the due date and time for the next medication dose administration, reminders of when the next medicament dose should be administered and may indicate appropriate possibilities for the user to stop, for instance a rest area.

It is also possible for the navigation system to be comprised by device 300, or comprised by a separate navigation device. In this case the navigation system can be configured as described above, and the necessary information is either already received by the device 300 or communicated to the separate navigation device. This communication may be sent from the device 300, the smart key 400, or the vehicle 500.

FIG. 4 illustrates schematically a different system 250. In this system 250, the injection monitoring device 2 communicates directly with the smart key 400. In these embodiments the smart key 400 is programmed with the medical monitoring application described above. The smart key 400 may therefore receive dosing information from the injection monitoring device 2 directly, the dosing information comprising at least a date and time of the most recent injection and data representing the administered medicament dose. The injection device 2 may be configured to transmit the dosing information to the smart key 400 whenever a new injection is performed, or alternatively only in response to a user input.

The smart key 400 may therefore use the medical monitoring application to store and manage the user dose history. The medical monitoring application is configured to use the stored dose history to determine a due time for the user's next medication dose. The smart key 400 may perform a plausibility check on the received data by communicating with the injection monitoring device 2 to confirm the accuracy of the information stored. The medical monitoring application may also infer a physiological condition of the user by comparing the current time with the determined due time for the next medication dose, as previously described. The user's physiological condition may be expressed in terms of their fitness to drive a vehicle.

The smart key 400 then communicates some or all of this information directly to the vehicle 500.

For example, the smart key 400 may determine a fitness of the user to drive, and communicate only this information to the vehicle 500. Alternatively, the smart key 400 may communicate the due time for the user's next medicament dose to the vehicle and the electronic warning system of the vehicle may perform the comparison. The smart key 400 may also have a small display screen. This screen can be used to present information to the user, including the due time for their next medication dose administration and any warnings should the current time be later than the determined due time. Whenever the smart key 400 is in range of the vehicle 500, or alternatively whenever the smart key 400 is used to unlock the vehicle 500, the smart key communicates the fitness of the user to drive and/or the due time to the electronic warning system of the vehicle 500. The electronic warning system of the vehicle 500 may then behave as described above with reference to FIG. 3.

The smart key 400 may continue to check the plausibility of the stored data after the vehicle 500 is started, i.e. during driving. If during driving, the time for the user's next medicament dose becomes due, then the electronic warning system of the vehicle 500 may notify the driver.

Figure 5:
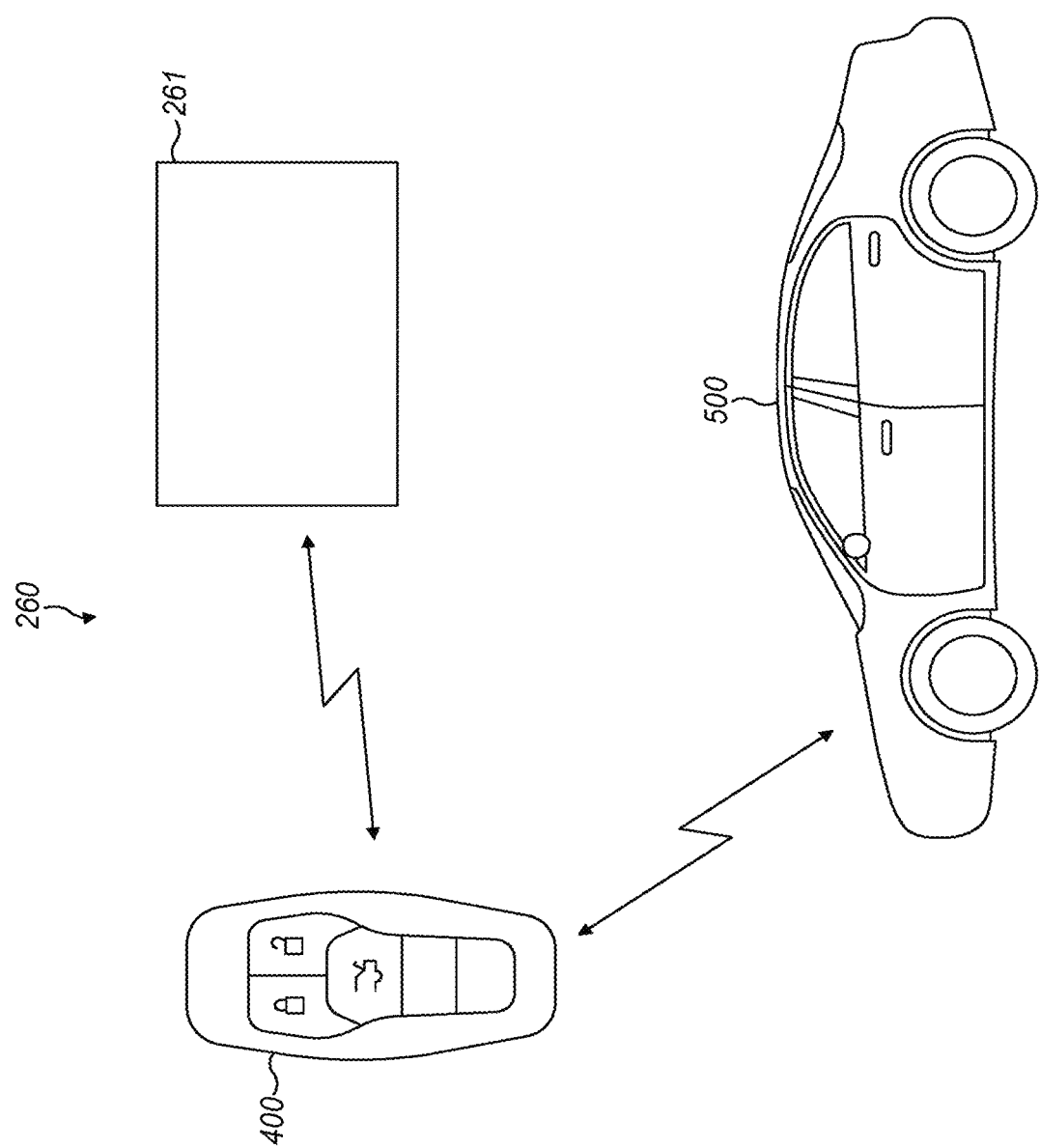
FIG. 5 is a schematic illustration of a system in which the present disclosure can be used, showing an example of a system including a continuous blood glucose meter, a smart key, and a vehicle.

FIG. 5 illustrates schematically a different system 260. In this system 260, the medical device is a permanent monitoring device 261 that is capable of continuously or regularly monitoring a condition, such as a physiological condition, of a user. For instance, the permanent monitoring device 261 may be a device that detects blood glucose levels either directly or indirectly.

Alternatively, the permanent monitoring device 261 may be a device that monitors the user's blood pressure and/or pulse.

At least a part of the information gathered by the permanent monitoring device 261, for instance including the user's condition or physiological condition, may then be communicated directly with the smart key 400. In these embodiments the smart key 400 is programmed with the medical monitoring application described above. The smart key 400 may therefore receive information, such as blood glucose levels, from the permanent monitoring device 261 directly. The permanent monitoring device 261 may be configured to transmit the information to the smart key 400 whenever a new measurement is performed, or whenever a deviation from a previous condition is detected.

The smart key 400 may use the medical monitoring application to store and manage a history of the user's condition. The medical monitoring application may be configured to use the stored history to determine an inference of a user's fitness to drive a vehicle. The medical monitoring application may be configured to use the stored history to determine a due time for the user's next medication dose; for instance, blood glucose levels may allow the medical monitoring application to determine when the next insulin dose should be delivered.

The smart key 400 then communicates some or all of this information directly to the vehicle 500. For example, the smart key 400 may determine an inference of the fitness of the user to drive, and communicate only this information to the vehicle 500. Alternatively, the smart key 400 may communicate the user's physiological condition, or the estimated due time for the next dose, to the vehicle and the electronic warning system of the vehicle may perform the comparison. The smart key 400 may also have a small display screen. This screen can be used to present information to the user, including their physiological condition, the estimated time for the next dose, their fitness to drive, and any warnings should they be unfit to drive. Whenever the smart key 400 is in range of the vehicle 500, or alternatively whenever the smart key 400 is used to unlock the vehicle 500, the smart key may communicate the fitness of the user to drive and/or the user's condition to the electronic warning system of the vehicle 500. The electronic warning system of the vehicle 500 may then behave as described above with reference to FIG. 3. For instance, the user may be provided with a warning relating to their impairment to drive or may be provided with advice relating to alleviating their condition. The advice may include reminders in relation to medicament doses or any other recommended steps.

The smart key 400 may communicate the user's condition to the vehicle 500 after the vehicle 500 is started, i.e. during driving. If during driving, the user's condition changes or if the user is determined to be unfit to drive, then the electronic warning system of the vehicle 500 may notify the driver and/or provide with advice relating to alleviating the user's condition. The vehicle 500 may be configured to reduce speed slowly and/or stop based on the received information or received instructions from the smart key 400 and/or medical device. For instance, the vehicle 500 can comprise safety assistant systems such as a lane assistant, to control the directional stability using a camera, and a speed assistant to control the vehicle speed. The safety assistant systems may be controlled based upon the information or instructions received from the smart key 400 and/or medical device. The vehicle 500 may be able to activate hazard lights, headlights (dipped or high beam), and/or activate any audible warning such as a vehicle horn based upon the information or instructions received.

The smart key 400 may be able to initiate an emergency call, for instance the smart key 400 may be able to communicate with an external communication device either directly or via the vehicle 500. Where communication is via the vehicle 500, this may utilize the vehicle's existing connection to a mobile communication device, such as a "hands-free" system. Where an emergency call has been initiated, the smart key 400 may be able to communicate relevant information, such as the condition of the user, the user's name, the medical disorder from which the user suffers, the type of medicament used by the user, the dose history, the history of the user's physiological condition, and any combination thereof.

In an illustrative example, a user who suffers from diabetes may be fitted with a connectable blood glucose monitoring (BGM) device. The BGM device communicates with a medical monitoring application which has been installed upon a smart key, and the communication comprises the user's blood glucose level. The medical monitoring application receives this information and performs a comparison in order to determine if the user is, for instance, hypoglycemic. If the medical monitoring application infers that the physiological condition of the user renders them unfit to drive, a communication will be sent to a vehicle. The communication comprises instructions to display a warning to the user. In addition, the vehicle may display advice to the user via the internal display screen, in this case the advice may include the advice to consume food or drink likely to alleviate the user's condition, including food or drink comprising sugar, fruit, chocolate, orange juice, or the like. If the vehicle is stationary and the user's condition is of a pre-determined level of severity the medical monitoring application sends instructions to the vehicle so that the engine is not allowed to start. If the vehicle is in motion and the user's condition is of a pre-determined level of severity, the medical monitoring application sends a communication to the vehicle to cause the safety assistant systems of the vehicle to slowly bring the vehicle to a stationary positon, to start the hazard lights, to sound the vehicle horn, and to initiate an emergency telephone call including the condition of the user, the user's blood glucose level, the user's name, the type of insulin used by the user, and last dose of insulin received.

In another illustrative example, a user taking painkillers, for instance a COX-2 inhibitor, may be monitored by medical devices such as a blood pressure gauge and/or a pulse meter. These medical devices communicate with a medical monitoring application which has been installed upon a smart key, and the communication comprises the user's physiological condition. Based on the physiological condition the medical monitoring application may perform any action described above.

Figure 6:
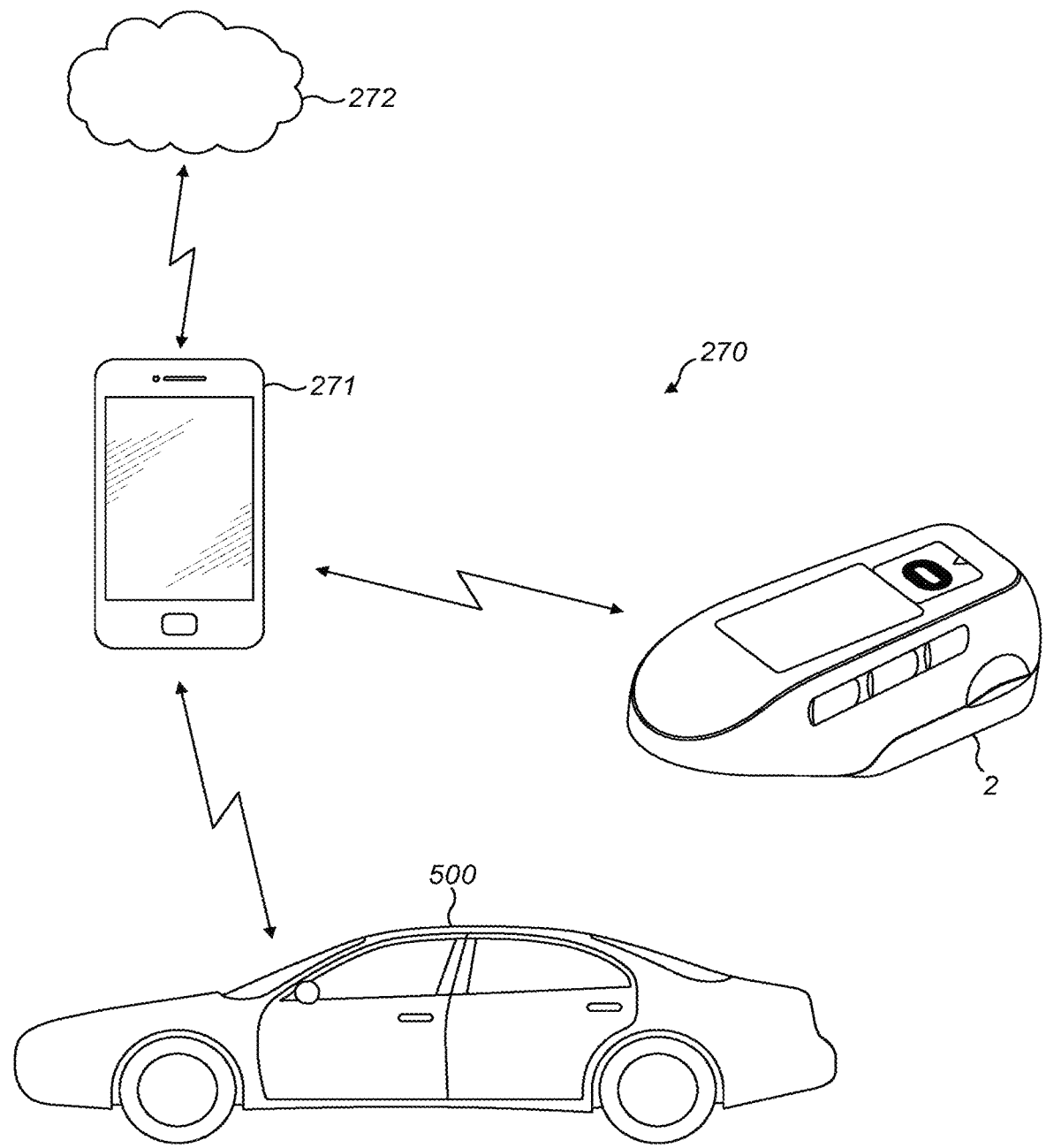
FIG. 6 is a schematic illustration of a system in which the present disclosure can be used, showing an example of a system including: a device such as a smart phone comprising an App, an intelligent medical device or a supplementary device for such a medical device, remote storage services, and a vehicle.

FIG. 6 illustrates schematically a different system 270. In this system 270, the medical device 2 communicates wirelessly with a device 271. The device 271 may for example be a smartphone storing a medical monitoring application described above and also storing an application that enables communication with a vehicle.

The medical monitoring application may be programmed to receive information from the medical device 2. The information may include dosing information comprising at least a date and time of the most recent injection and data representing the administered medicament dose, and/or may include information comprising the user's condition or physiological condition. The medical device 2 may be configured to transmit the information to the device 271 whenever a new injection or measurement is performed, when a deviation from a previous condition is detected, or alternatively only in response to a user input.

The device 271 may communicate the information to remote storage 272. For instance, the remote storage 272 may be a cloud storage service. The remote storage 272 may be used to store and manage a history of the user's condition and dose history. The device 271 may be able to access the remote storage 272 in order to receive previous information including the time and date of any medicament doses, the type of medicament, the medicament dose quantity, or any recorded physiological conditions. The device 271 may also be able to access the remote storage 272 in order to receive the calculated or defined due time for the user's next medicament dose. The device 271 may be able to access the remote storage 272 in order to receive data indicating an inferred physiological condition of the user by comparing the current time with the determined due time for the next medication dose, as previously described. The device 271 may be able to access the remote storage 272 in order to receive data indicating the user's fitness to drive a vehicle.

The device 271 then communicates some or all of this information directly to the vehicle 500. For example, the device 271 may communicate a fitness of the user to drive to the vehicle 500. Alternatively, the device 271 may communicate the due time for the user's next medicament dose to the vehicle and the electronic warning system of the vehicle may perform the comparison. The vehicle 500 may then behave as described above with reference to FIG. 3, 4, or 5.

The device 271 may also have a display screen which can be used to present information to the user, including the due time for their next medication dose administration and any warnings should the current time be later than the determined due time.

Figure 7:
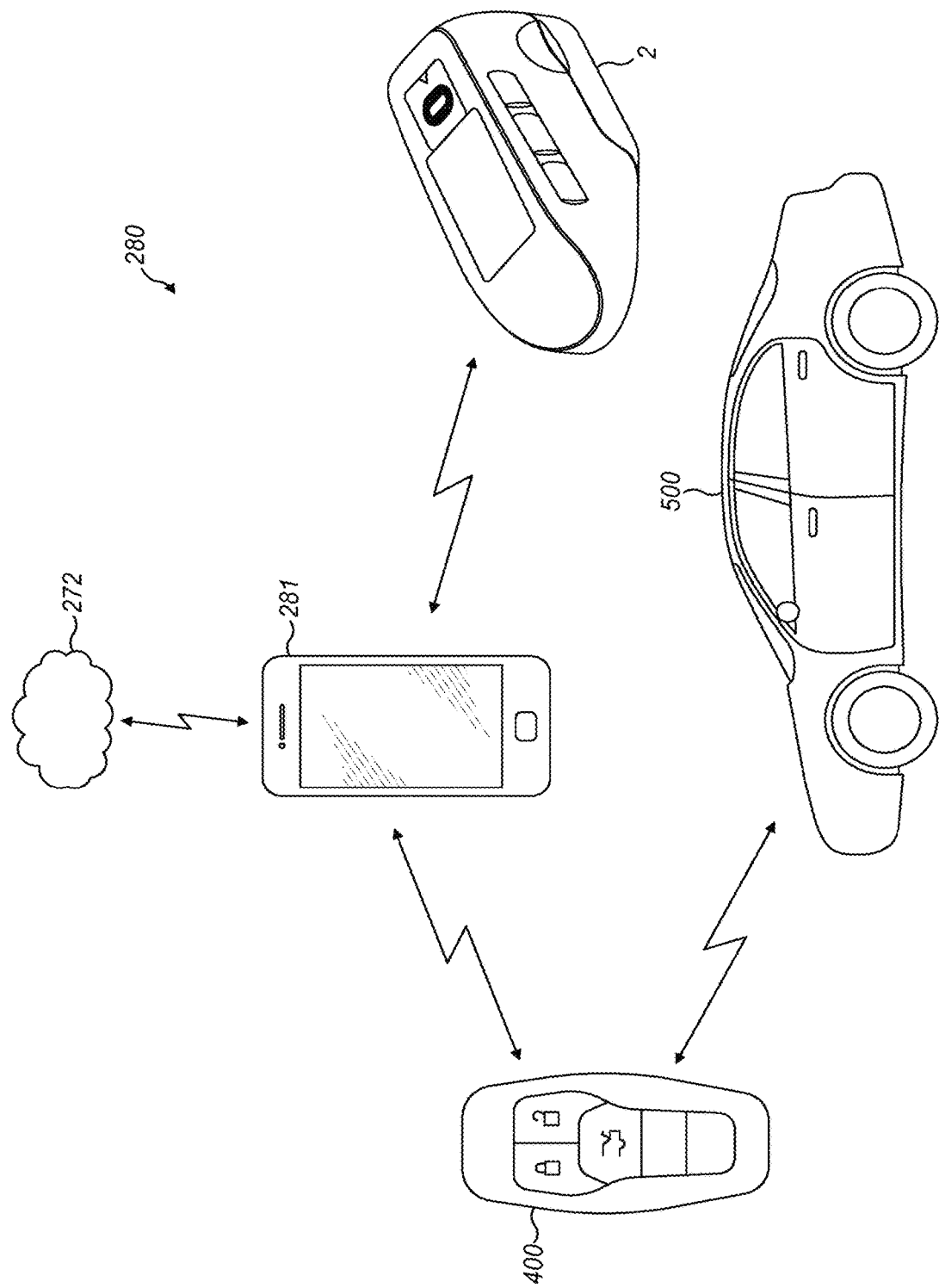
FIG. 7 is a schematic illustration of a system in which the present disclosure can be used, showing an example of a system including: a device such as a smart phone comprising an App, an intelligent medical device or a supplementary device for such a medical device, a smart key, remote storage services, and a vehicle.

FIG. 7 illustrates schematically a different system 280. In this system 280, the medical device 2 communicates wirelessly with a device 281. The device 281 is able to communicate with both a smart key 400 and remote storage 272, which may be a cloud storage service.

In some aspects, the system 280 operates similarly to that described in relation to FIG. 3. However, device 281 may communicate the information received from the medical device 2 to the remote storage 272. The remote storage 272 may be used to store and manage a history of the user's condition and dose history. The device 281 may be able to access and communicate with the remote storage 272 in the manner described for FIG. 6.

Figure 8:
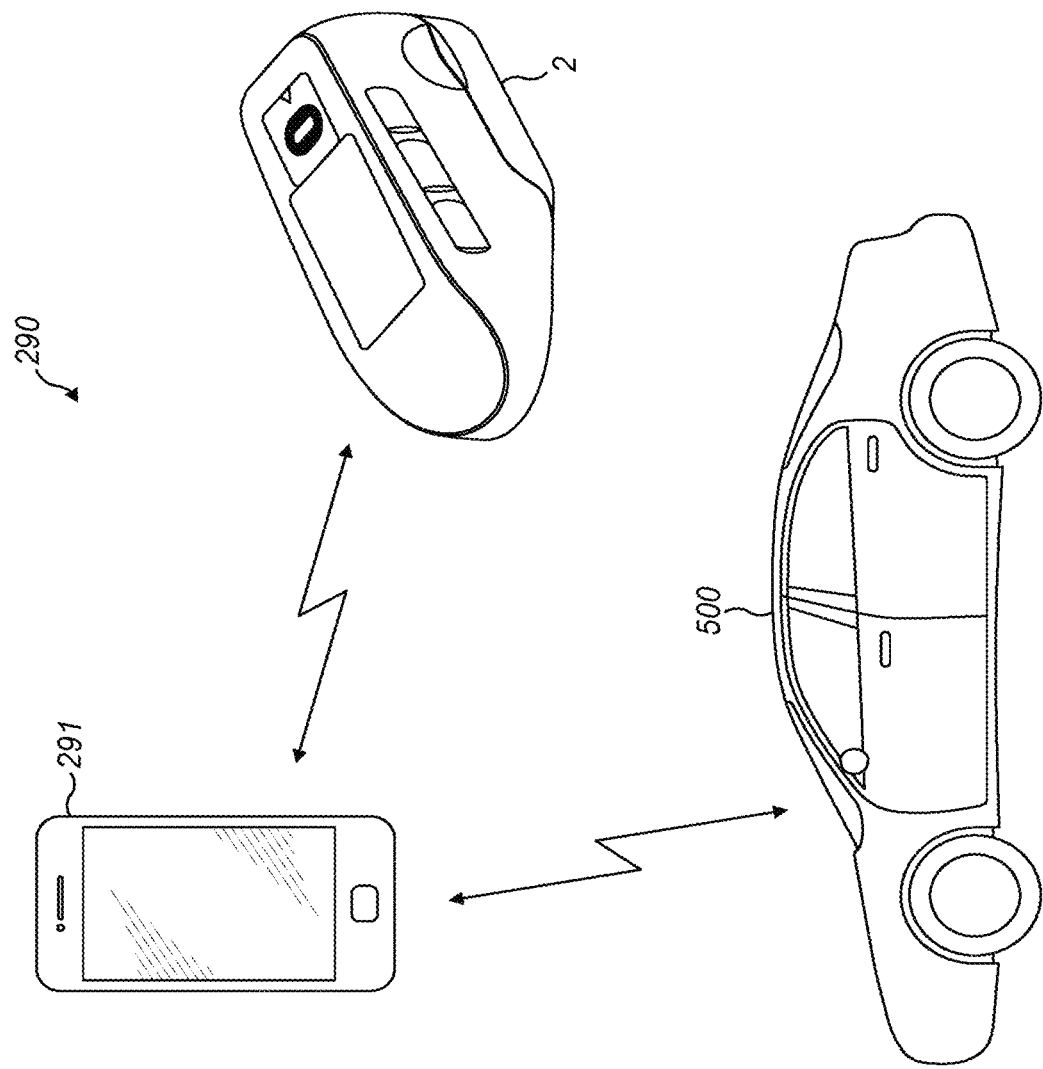
FIG. 8 is a schematic illustration of a system in which the present disclosure can be used, showing an example of a system including: a device such as a smart phone comprising an App, an intelligent medical device or a supplementary device for such a medical device, and a vehicle.

FIG. 8 illustrates schematically a different system 290. In this system 290, the medical device 2 communicates wirelessly with a device 291. The communication between the medical device 2 and the device 291 is the same as described in relation to FIG. 3 above. The content of the information communicated to the vehicle 500, and the vehicle's corresponding actions, are also the same as described in relation to FIG. 3 above. However, device 291 is able to directly communicate with vehicle 500, and may comprise an application for communication with vehicle 500. This communication may be a wireless or wired communication, optionally this communication is via Bluetooth. This communication may, for instance, be via an existing mechanism for pairing a smart phone with an entertainment system of a vehicle.

For the systems described above, once the user's fitness to drive has been inferred, the information may be categorized under "driving ability level" categories. These categories may vary by severity, for instance a first category may be assigned to users who are fit to drive. A second category may be assigned to users who may be suffering from mild impairment. A third category may be assigned to users who are suffering from severe impairment. Further categories are envisaged indicating varying severity. The device or smart key may be configured to send different instructions depending on the category to which the user's driving ability level has been assigned. The vehicle may be configured to perform different actions depending on the category to which the user's driving ability level has been assigned. For instance, the vehicle may emit warnings to user's in the second category, whereas may prevent users in the third category from driving or activate safety assistant systems as described above.

Examples above relating to diabetic patients who require insulin are illustrative. The present disclosure is also applicable to any users who may become impaired. For instance, patients who require cardiovascular medication or patients who require painkillers, such as a COX-2 inhibitor.

While some examples of the injection monitoring device 2 are shown herein, the systems described above can be configured to work with any device configured to monitor the amount or dosages of medicament administered to a patient. For example, the above systems can accommodate injection devices having integrated injection monitoring solutions (e.g., injection devices which include an integrated dose monitoring solution carried on-board the injection device) as well as other types of injection monitoring devices meant to be retrofitted or added-on to existing injection devices (e.g., add-on injection monitoring devices which fit over and/or partially or completely encapsulate the injection button 11 of the injection device 1). The systems described above can also accommodate one-time use or disposable injection devices that include their own integrated injection monitoring devices.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin. Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A supplementary device comprising:
a sensor configured to measure or determine an injection history of an injection device when the supplementary device is attached to the injection device, the injection history being indicative of a past injection of a medicament from the injection device for a patient;
a processor configured to determine future injection information based on the injection history, the future injection information being indicative of a time for a future injection of the medicament or a volume of the future injection; and
a wireless unit configured to transmit the future injection information to one or more external devices,
wherein the supplementary device is configured to be releasably attached over a button of the injection device, and the sensor is configured to measure a position or a movement of the button.

2. The supplementary device of claim 1, wherein the supplementary device is configured to be releasably attached to a side of a housing of the injection device, and the sensor is configured to measure a position or a movement of a dose dial of the injection device.

3. The supplementary device of claim 1, wherein the supplementary device is configured to be releasably attached to a side of a housing of the injection device, and the sensor is configured to read a dose indicator of a dose dial of the injection device.

4. The supplementary device of claim 1, wherein the sensor is configured to determine the injection history based on a position or a movement of one or more components of the injection device relative to the supplementary device.

5. The supplementary device of claim 4, wherein the sensor is configured to measure the position or the movement of the one or more components of the injection device relative to the supplementary device without requiring direct contact between the sensor and the one or more components.

6. The supplementary device of claim 1, wherein the one or more external devices are configured to transmit control signals to a vehicle for controlling one or more operations of the vehicle based on the future injection information.

7. The supplementary device of claim 6, wherein the one or more external devices comprise a smart key configured to transmit the control signals to the vehicle for controlling the one or more operations of the vehicle based on the future injection information, the one or more operations configured to be controlled when the patient is an occupant of the vehicle.

8. The supplementary device of claim 1, wherein the one or more external devices are configured to transmit information to a vehicle for providing an indication of the future injection information when the patient is an occupant in the vehicle.

9. The supplementary device of claim 1, comprising an alert system configured to provide an indication of the future injection information.

10. A supplementary device comprising:
a first sensor configured to measure or determine an injection history of an injection device when the supplementary device is attached to the injection device;
a processor configured to determine a due time for an injection of a medicament based on the injection history; and
a wireless unit configured to transmit the due time to one or more external devices,
wherein the supplementary device is configured to be releasably attached over a button of the injection device, and the first sensor is configured to measure a position or a movement of the button.

11. The supplemental device of claim 10, wherein the one or more external devices are configured to determine a wellness of a patient based on the due time, the wellness being indicative of an impairment of the patient or an inability of the patient to drive a vehicle.

12. The supplementary device of claim 11, wherein the one or more external devices are configured to transmit control signals to the vehicle for controlling one or more operations of the vehicle based on the wellness of the patient.

13. The supplementary device of claim 12, wherein the one or more external devices are configured to determine a severity of the impairment of the patient, and the vehicle is configured to control the one or more operations of the vehicle based on the severity of the impairment.

14. The supplementary device of claim 13, wherein the one or more external devices are configured to determine the severity of the impairment by selecting a level of severity from at least three levels of severity.

15. The supplementary device of claim 11, comprising a second sensor configured to measure or determine information identifying the medicament, and the processor is configured to compare the information identifying the medicament to stored information to verify that the medicament is for the patient.

16. The supplementary device of claim 15, wherein the second sensor comprises a camera, a QR reader, or a barcode reader, and the information identifying the medicament of the injection device comprises a barcode or a QR code configured to be read by the camera, the QR reader, or the barcode reader of the supplementary device.

17. The supplementary device of claim 10, wherein the one or more external devices comprise one or more mobile devices configured to communicate with a vehicle for controlling one or more operations of the vehicle based on the due time.

18. The supplementary device of claim 17, wherein the injection history comprises a date and a time of a past injection and a volume of the medicament administered in the past injection.

19. The supplementary device of claim 10, comprising an alert system configured to provide an indication of the due time, the alert system comprising at least one of a speaker or a display.

* * * * *